United States Patent [19]

Storey, Jr. et al.

[11] Patent Number: 5,033,462
[45] Date of Patent: Jul. 23, 1991

[54] INTRAORAL TRAUMA DRESSING

[76] Inventors: Fredrick G. Storey, Jr.; Carol W. Scott, both of P.O. Box 552, Marshall, Va. 22115

[21] Appl. No.: 151,905

[22] Filed: Feb. 3, 1988

[51] Int. Cl.⁵ .............................................. A61F 13/00
[52] U.S. Cl. .................................... 128/156; 433/136; 433/137
[58] Field of Search ...................... 128/155, 156, 115.1, 128/849-857, 859-860, 862, DIG. 23; 604/370, 371, 362; 433/136, 137, 138; 623/8

[56] References Cited

U.S. PATENT DOCUMENTS

| | | | |
|---|---|---|---|
| 3,698,393 | 10/1972 | Stone | 604/362 |
| 3,736,935 | 6/1973 | Reimels . | |
| 4,068,666 | 1/1978 | Shiff . | |
| 4,372,314 | 2/1983 | Wall . | |
| 4,543,098 | 9/1985 | Wolfe et al. . | |
| 4,568,326 | 2/1986 | Rangaswamy . | |

Primary Examiner—Randall L. Green
Assistant Examiner—Paul Prebilic
Attorney, Agent, or Firm—Foley & Lardner

[57] ABSTRACT

A trauma dressing suitable for intraoral use, comprising an absorbent dressing to which is attached a retrieval strand, with the retrieval strand being sufficiently rigid to prevent collapse into the oral cavity of a patient, and the retrieval strand having a first end attached to the dressing and a second end which is sufficiently large so as to prevent entry into the oral cavity of the patient. Preferably, the retrieval strand is made of a plastic material and has a substantially T-shaped end attached to the dressing and a substantially ring-shaped end to prevent entry into the oral cavity of a patient. The free end of the retrieval strand may be attached outside the oral cavity to an attachment member such as an extrication collar.

23 Claims, 4 Drawing Sheets

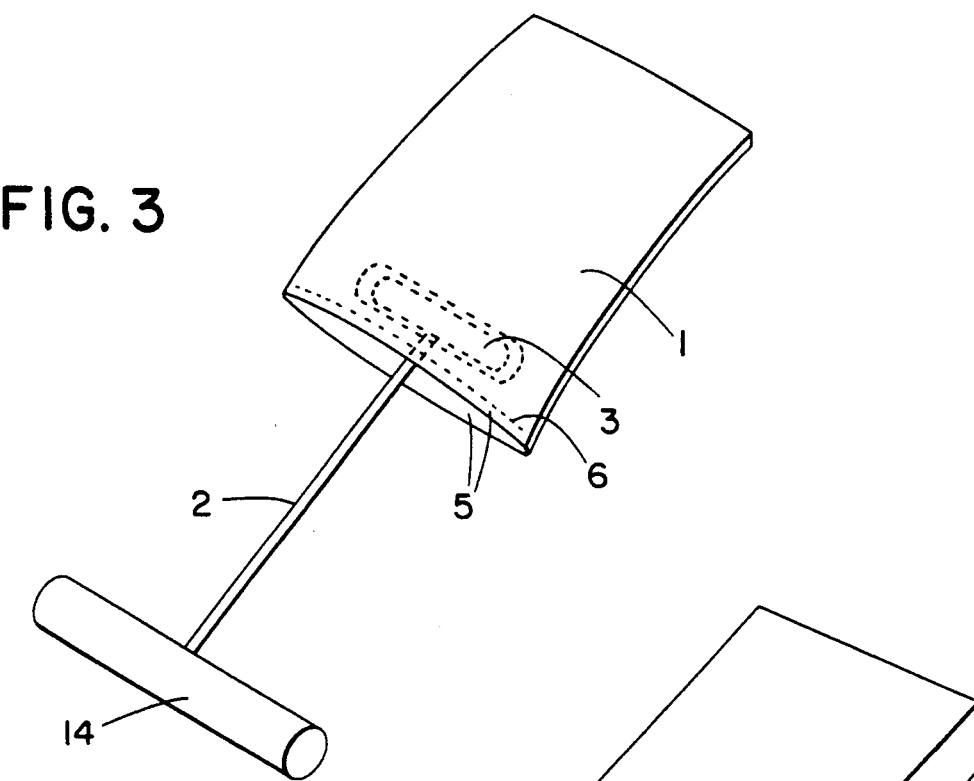
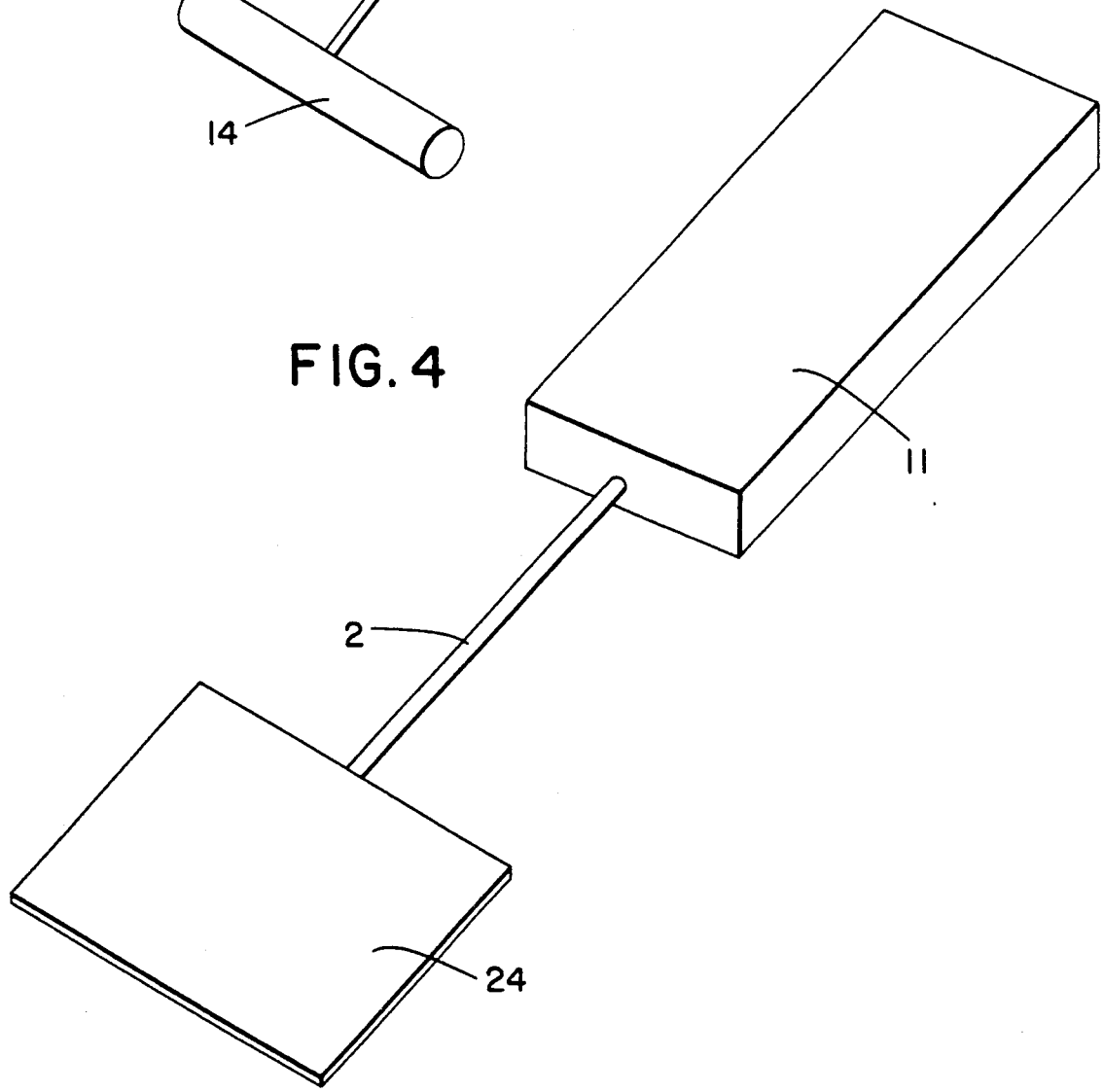

INTRAORAL TRAUMA DRESSING

BACKGROUND OF THE INVENTION

This invention relates to trauma dressings, and more particularly, to trauma dressings suitable for intraoral use.

Traumatic injuries to the face and oral cavity have always presented treatment problems due to the importance of maintaining in the victim a free and unobstructed airway. It has not been the practice in treating oral or facial injuries in the field to use any kind of dressing or sponge intraorally because of the danger that the victim may aspirate the dressing or sponge, causing asphyxiation. Due to the poor accessibility of the location, it can be very difficult to extract a dressing which has become lodged in a patient's airway. Consequently, use of absorbent dressings intraorally has been avoided, and it has been necessary to rely on suction to prevent particulates or blood from blocking the airway. However, suction alone is inadequate to prevent blood loss and resulting hypovolemic shock.

Surgical sponges are known to the art which have loops or strings attached to them. Examples include the devices disclosed in Stone, U.S. Pat. No. 3,698,393; Reimels, U.S. Pat. No. 3,736,935; and Shiff, U.S. Pat. No. 4,068,666. However, none of these are suitable for intraoral use. Moreover, their retrieval loops or strings are limp and can collapse inside the patient's oral cavity.

Similarly, absorbent tampons are known which have attached withdrawal strings. For example, see Wolfe et al., U.S. Pat. No. 4,543,098. These devices are subject to all the same disadvantages of the aforementioned surgical sponges.

Special dental sponges have been designed for intraoral use in conjunction with dental surgery. See, for example, Wall, U.S. Pat. No. 4,372,314; which discloses a variety of such devices. Also, a special epistaxis sponge with a relatively rigid handle for intranasal use in treating nosebleeds is disclosed in Rangaswamy, U.S. Pat. No. 4,568,326. Due to the special configurations of these devices, however, they are not suitable for treating intraoral injuries due to facial or oral trauma.

There is a need for a dressing which may be used intraorally in treatment of facial or oral trauma without compromising the safety of the victim or the effectiveness of the dressing.

SUMMARY OF THE INVENTION

It is accordingly an object of the present invention to provide a dressing or sponge which is suitable for intraoral use in treating oral and facial traumas.

It is another object of the present invention to provide a dressing for intraoral use which has means for preventing aspiration into a patient's airway and thereby avoids the threat of blocking the patient's airway.

It is still another object of the present invention to provide a dressing for intraoral use which has a means which enables attending medical personnel to easily visually determine if a dressing is in place.

Still another object of the invention is to provide an absorbent dressing for intraoral use which can be readily extracted if it becomes dislodged from its intended position in the oral cavity and obstructs the patient's airway.

A further object of the invention is to provide an intraoral trauma dressing system which makes it possible to secure an intraoral dressing externally of the oral cavity and also facilitates an accurate accounting of intraoral dressings which are used.

These and other objects of the invention are achieved by providing a trauma dressing for intraoral use, comprising an absorbent dressing for insertion into the oral cavity of a patient, a flexible, self-sustaining retrieval strand having one end securely attached to said absorbent dressing, and an enlarged grip member of sufficient size to prevent its entry into the oral cavity attached to the other end of said retrieval strand.

BRIEF DESCRIPTION OF THE DRAWINGS

FIG. 3 illustrates one method of attaching the retrieval strand to the absorbent dressing of the trauma dressing of FIG. 1;

FIG. 4 is a perspective view of an alternate embodiment of the trauma dressing of the present invention;.

DETAILED DESCRIPTION OF PREFERRED EMBODIMENTS

The intraoral dressing and dressing system of the present invention will be described with reference to preferred embodiments illustrated in FIGS. 1 through 7.

Figure 1:
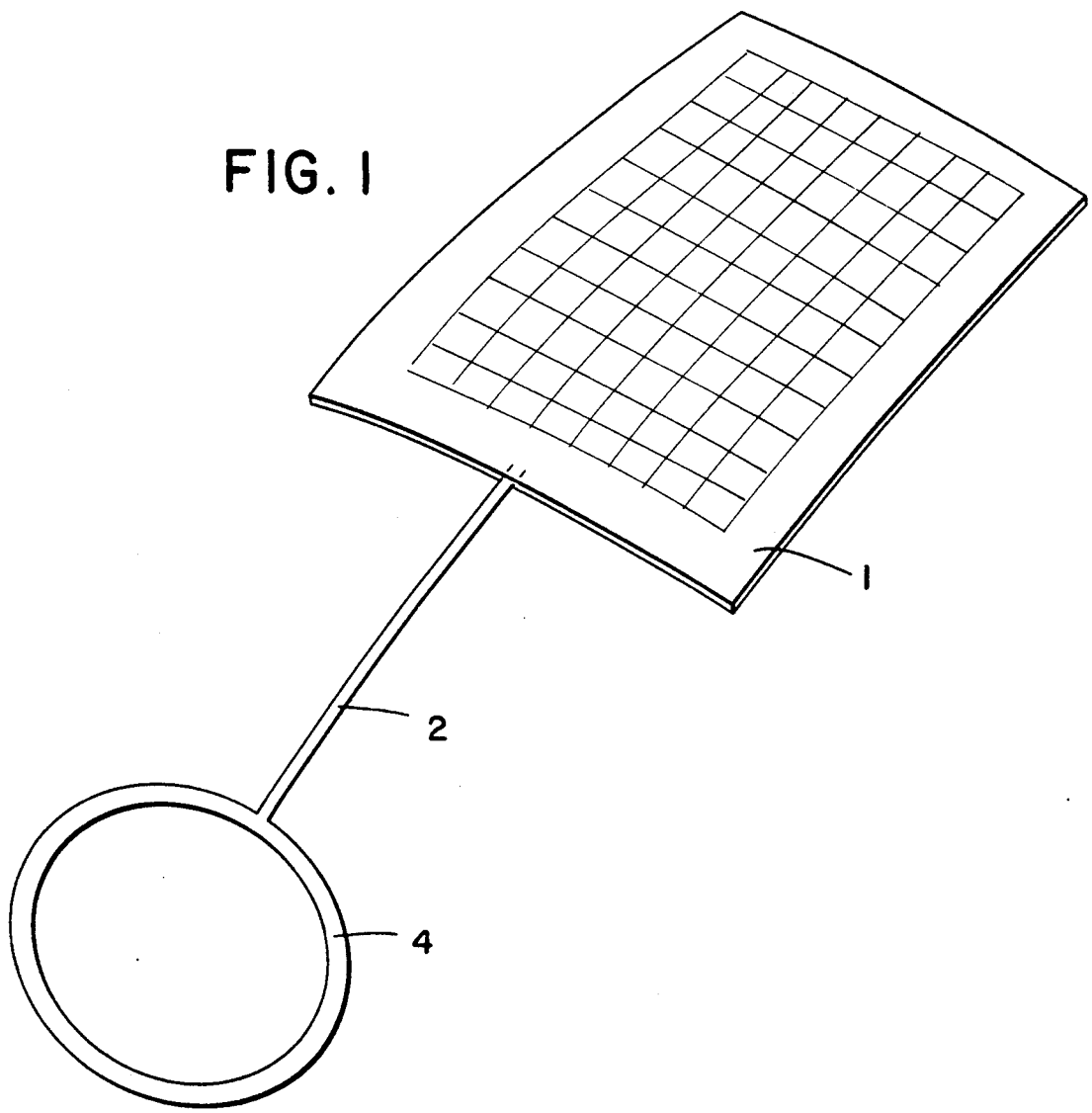
FIG. 1 is a perspective view of a first embodiment of a trauma dressing according to the present invention.

As illustrated in FIG. 1, an absorbent dressing 1 is attached to one end of a retrieval strand 2. The other end of retrieval strand 2 is connected to an enlarged grip member 4.

Absorbent dressing 1 may take a variety of configurations. For example, conventional gauze pads, cotton wads, or non-woven dressings may be used. Loose filaments or fibers and frayed or free floating strands should be avoided to prevent them from causing a gag reflex or from wicking blood away from the trauma site. The size of absorbent dressing 1 should be such that it can be readily inserted into a desired position inside the oral cavity of a victim of facial or oral trauma. Of course, the dressing must be sterile to avoid infecting the wound.

Retrieval strand 2 must be flexible, yet self-supporting. As used herein, the term "flexible" is intended to mean that the retrieval strand is sufficiently bendable that it does not interfere with desired positioning of the absorbent dressing inside the oral cavity. The term "self-supporting" is intended to mean that the material is sufficiently rigid or semi-rigid, that it will generally maintain an extended position under the influence of its own weight. In other words, it must be sufficiently self-supporting that it will not collapse into the oral cavity like a limp string or band.

Grip member 4 must be of sufficient size that it will not be drawn into the oral cavity of a patient. Although grips with a transverse dimension relative to the longitudinal direction of the retrieval strand of about two to two and one-half inches are generally of sufficient size, it is preferred that the grip member be at least three inches across to assure it cannot enter the oral cavity. It is convenient to use a four inch diameter plastic ring as the grip member for a dressing formed of standard four inch by four inch gauze pads. Generally the grip member will be less than five or six inches across so that its size will not interfere with convenient handling. Use of oversize grip members should also be avoided to reduce the possibility of snagging and inadvertent extrication.

Because it is readily visible to attending medical personnel and is connected to the absorbent dressing 1 by self-supporting retrieval strand 2, grip member 4 also provides a means for readily ascertaining whether the dressing is properly in place. If the position of the dressing shifts, this will generally be reflected by a shift in the position of the grip member. If desired, the grip member may be provided with distinctive coloration to increase its visibility. For example it could be colored fluorescent pink or marked with orange stripes to make it easier to see. Optionally, various sizes and/or configurations of dressings could be identified by distinctive color codes on the retrieval strands and/or grip members.

If desired, the retrieval strand and grip member may be formed separately of the same material or of different materials. It is advantageous, however, if the two parts are formed as a single integral piece. They may be made of any suitable material which: (1) is flexible, yet sufficiently rigid to be self-supporting; and (2) is capable of being sterilized to prevent introduction of any contamination to the injuries being treated. The retrieval strand itself should be sufficiently thick and free of sharp edges that it will not cut soft tissue. It must also be formed of a material which is sufficiently soft that it will not break teeth if bitten, and yet it must be sufficiently strong that it cannot be bitten through. In a preferred embodiment, retrieval strand 2 and grip member 4 may be made of a thermoplastic material such as polyolefins, e.g. polyethylene, polypropylene, polyvinylchloride; polyamides, such as nylon; polyesters, such as polyethylene terephthalate; polyurethanes, or other similar plastic materials. They may be produced by conventional injection molding, extrusion and thermoforming, or other manufacturing processes.

Figure 2:
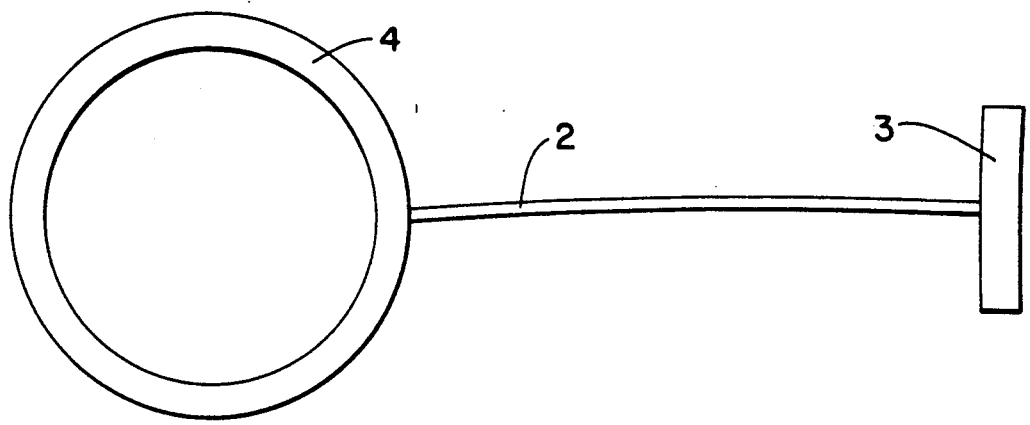
FIG. 2 is a perspective view of the retrieval strand and grip member of the trauma dressing of FIG. 1.

Although the retrieval means may comprise any material and have any shape which comports with its intended objects, a preferred embodiment is illustrated in FIG. 2. In this embodiment, the retrieval strand comprises a single filament of plastic material. Forming the retrieval strand as a thermoplastic monofilament has the advantage that it will not wick blood away from the trauma site. It should be understood, however, that multifilament arrangements may also be used.

One end of the strand is formed with an enlarged head 3 in order to facilitate attachment to the material of the absorbent dressing. The other end of retrieval strand is formed into an enlarged gripping ring 4. The ring shape is especially convenient, but if desired, the grip member can take the shape of a flat tab, a cross-bar or any other desired configuration so long as it is of sufficient size that it will not enter the oral cavity of a patient. The size and shape of the grip member should be such that it can be easily secured outside of the oral cavity to an extrication collar or other applicance. Three dimensional shapes are also possible, but are typically less convenient to package and may be less readily secured externally of the oral cavity.

One method of attaching the retrieval strand 2 to the dressing is illustrated in FIG. 3. In this embodiment, dressing 1 is formed of multiple layers 5, and the enlarged head 3 of the retrieval strand is inserted between the layers. The layers of the dressing are then stitched together along dotted line 6 to prevent the enlarged head from being withdrawn. As shown in the drawing, the line of stitching is extended all around the head of the retrieval strand to hold it securely in position, but this is optional under most circumstances. This method of attachment is practical and results in secure attachment of the retrieval means with the fibers of the dressing.

Alternatively, the head of the retrieval strand could be thermally welded, e.g. laser welded, or adhesively bonded to the fibers of the absorbent dressing to attach the strand to the dressing. Adhesives which are used must, of course, be non-toxic and must also be insoluble in saliva, mucous or other bodily fluids. Any method which results in secure interlaced or interlocked attachment of the retrieval strand to the absorbent dressing is intended to be within the scope of the invention.

FIG. 3 also illustrates a gripping member formed as an enlarged cross bar 14. The resilience of the retrieval strand is generally sufficient to prevent the cross bar grip from twisting 90 degrees and entering the oral cavity endwise.

The shape of the dressing may be varied as desired in order to provide the maximum number of possibilities to deal with the variety of traumatic injuries encountered in the field. Generally the absorbent dressing will be sufficiently thin and flexible that it can be readily folded or compressed in order to fit in any desired location within the oral cavity of a patient. Although most conventional dressings are substantially flat and square or rectangular in shape, other configurations are possible. One alternate embodiment of the invention is illustrated in FIG. 4. This dressing 11 is similar in its details of construction to previously described embodiment and differs only in being thicker and having an elongated shape in order to facilitate positioning along the gum line in the oral cavity. The embodiment illustrated in FIG. 4 also differs in having a grip member which is formed as an enlarged flat tab 24. Of course, there is no limit to the number of dressing shapes or grip member shapes which may be constructed within the scope of the present invention.

If after placement in the oral cavity of a patient, the dressing of the invention becomes dislodged from its intended position and wholly or partially obstructs the patient's airway, this can be quickly and easily detected by attending medical personnel from the position of the grip member. The dressing can then be promptly and reliably either withdrawn from or repositioned in the patient's oral cavity by grasping the grip member and pulling. The dressing of the invention can thus be used safely to staunch intraoral bleeding of victims of oral or facial trauma.

As alluded to above, it is desirable to secure the retrieval strands externally of the oral cavity. This not only reduces the possibility of accidental displacement, e.g. by snagging the retrieval strand or grip member, but it also facilitates retention of the dressings even after withdrawal from the oral cavity so that all the dressings used may be readily accounted for. This may be helpful, for example, to assist later assessment of blood loss by emergency room personnel. In order to achieve this, the invention also contemplates a trauma dressing system for intraoral use comprising an absorbent dressing for insertion into the oral cavity of a patient, a flexible, self-sustaining retrieval strand having one end securely attached to the absorbent dressing, an attachment member securable to patient outside the oral cavity, and means for attaching the retrieval strand to the attachment member.

Figure 5:
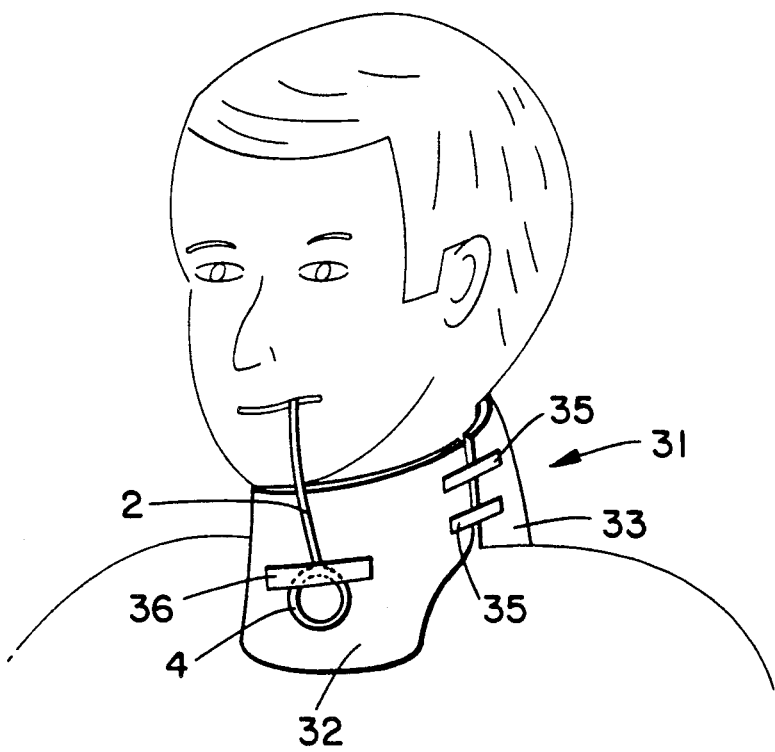
FIG. 5 is a perspective view of an intraoral trauma dressing system in which the dressing is secured externally of the oral cavity.

The attachment member may be any type of secure external appliance or even an article of clothing. FIG. 5 illustrates a particularly preferred embodiment of the invention in which the attachment member is an extrication collar. It is known to apply a supporting collar to the neck of a trauma victim before attempting to move the victim in order to prevent aggravation of possible injuries to the spinal column. Such collars are commonly referred to as extrication collars. A collar of this type, identified generally by reference numeral 31, is illustrated in FIG. 5. Collar 31 is formed of a supportive foam core covered by a soft fabric cover and comprises front and back sections 32 and 33, respectively, connected to each other by releasable fastener strips 35, e.g. Velcro ™ fasteners. Collar 31 is designed to fit securely around the neck and over the shoulders of a patient to support the head and neck.

FIG. 5 also shows a retrieval strand 2 of an intraoral dressing protruding from the mouth of a human patient. The absorbent dressing is, of course, out of view inside the patient's mouth. The distal end of retrieval strand 2 adjacent grip member 4 is secured by any suitable, attach to the front section 32 of the extrication collar. In the illustrated embodiment, this is most simply affected by a strip of adhesive tape 36.

Figure 6:
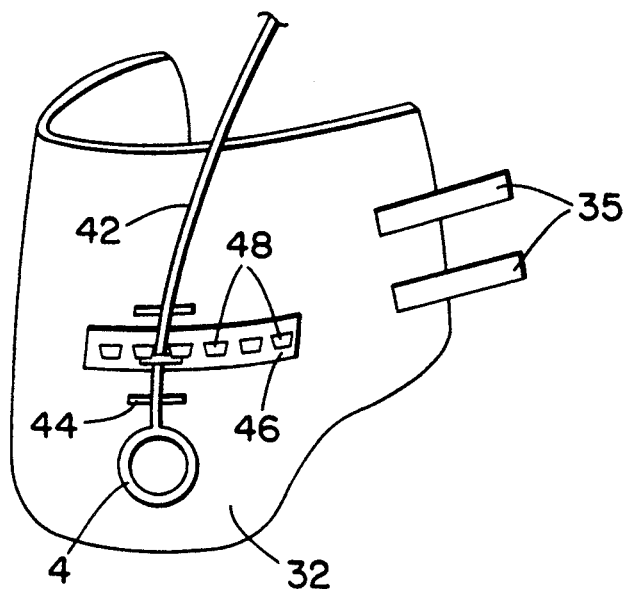
FIG. 6 is a perspective view of a first alternate system for securing an intraoral trauma dressing.

FIG. 6 shows a first alternate embodiment of the trauma dressing system of the invention in which retrieval strand 42 is provided with a plurality of cross bars 44 in addition to grip member 4. For convenience of illustration only three cross bars are shown, but it will appreciated that a greater or lesser number may be provided as desired. A desired one of the cross bars 44 is received underneath two adjacent protruding tabs 48 on a mounting strip 46 on front collar section 32 with strand 42 extending between the two tabs. Mounting strip 46 and tabs 48 may be formed of any desired resilient plastic material and are configured to hold the cross bar and strand in place, e.g. either by hooking around the cross bar or by having a constriction in the entrance to the space through which the strand passes between adjacent tabs. It will be appreciated that strand 42 can be secured at any desired point along its length depending only on the number of cross bars and on which of the bars is engaged by the tabs.

Figure 7:
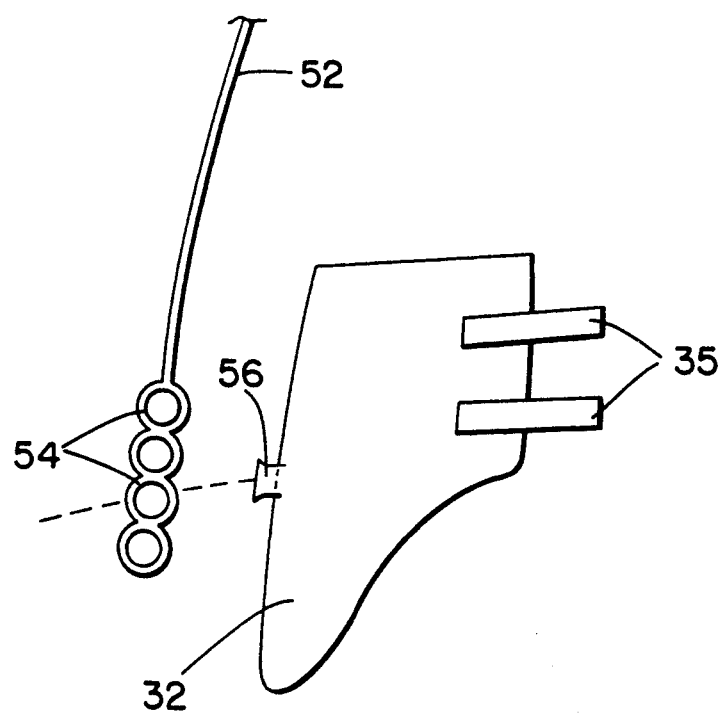
FIG. 7 is a side view of a second alternate system for securing an intraoral trauma dressing.

FIG. 7 shows a second alternate embodiment which is similar to the embodiment of FIG. 6 except that strand 52 is provided with a plurality of loops 54, a desired one of which can be secured on a button or post 56 on the front section 32 of the collar.

The retrieval strand must be of sufficient length to extend from the furthers reaches of the oral cavity to the attachment point on the extrication collar or other attachment member. Attachment lengths typically vary from about 6 inches to about 10 inches depending on the size of the patient and the location of the trauma. Good results may be achieved by forming cross bars, loops or other attachments at approximately one-half inch intervals along the strand, but longer or shorter spacings may also be used.

The foregoing description has been set forth merely to illustrate preferred embodiments of the invention and is not intended to be limiting. Since modifications of the described embodiments incorporating the spirit and substance of the invention may occur to persons skilled in the art, it is intended that the invention be construed to embrace everything within the scope of the appended claims and equivalents.

What is claimed is:

1. A trauma dressing for intraoral use comprising an absorbent dressing for insertion into the oral cavity of a patient, a flexible self-supporting retrieval strand having one end securely attached to said absorbent dressing, and an enlarged grip member of sufficient size to prevent its entry into the human oral cavity attached to the other end of said retrieval strand.

2. A trauma dressing as claimed in claim 1, wherein said retrieval strand comprises a single filament of thermoplastic material.

3. A trauma dressing as claimed in claim 1, wherein said absorbent dressing comprises a plurality of layers of absorbent material, and said retrieval strand is attached to said absorbent dressing by inserting an enlarged head at one end of said retrieval strand between adjacent layers and thereafter sewing the layers together in a manner to prevent extrication of said enlarged head from between them.

4. A trauma dressing according to claim 1, wherein said retrieval strand is adhesively bonded to fibers of said absorbent dressing.

5. A trauma dressing according to claim 1, wherein said retrieval strand is thermowelded to said absorbent dressing.

6. A trauma dressing according to claim 1, wherein said retrieval strand and said grip member are integrally formed as a single piece.

7. A trauma dressing according to claim 1, wherein said grip member is in the shape of a ring.

8. A trauma dressing according to claim 1, wherein said grip member is in the shape of a cross-bar.

9. A trauma dressing according to claim 1, wherein said grip member is in the shape of a flat tab.

10. A trauma dressing for intraoral use comprising an absorbent dressing for insertion into the oral cavity of a patient, a flexible, self-supporting retrieval strand having one end securely attached to said absorbent dressing, and an enlarged grip member of sufficient size to prevent its entry into the human oral cavity attached to the other end of said retrieval strand, and wherein said grip member has a width of at least three inches in a direction transverse to the longitudinal direction of said retrieval strand.

11. A trauma dressing according to claim 1, wherein said retrieval strand is formed of a thermoplastic material selected from the group consisting of polyolefins, polyurethanes, polyamides and polyesters.

12. A trauma dressing according to claim 1, wherein said absorbent dressing comprises a sterile gauze pad.

13. A trauma dressing according to claim 2, wherein the end of said retrieval strand attached to said absorbent dressing has a substantially T-shaped head.

14. A trauma dressing system for intraoral use comprising:
    (a) an absorbent dressing for insertion into the oral cavity of a human patient, with a flexible, self-supporting retrieval strand having one end securely attached to said absorbent dressing;
    (b) an attachment member securable to a patient outside the oral cavity; and
    (c) means for attaching said retrieval strand to said attachment member.

15. A trauma dressing system according to claim 14, further comprising an enlarged grip member of sufficient size to prevent its entry into the human oral cavity attached to the other end of said retrieval strand.

16. A trauma dressing system according to claim 14, wherein said attachment member is a collar.

17. A trauma dressing system according to claim 16, wherein said collar is a two-piece extrication collar.

18. A trauma dressing system according to claim 14, wherein said means for attaching comprises a strip of adhesive tape.

19. A trauma dressing system according to claim 14, wherein said means for attaching comprises at least one cross bar formed on said retrieval strand and a plurality of tabs on said attachment member for engaging said cross bar.

20. A trauma dressing system according to claim 14, wherein said means for attaching comprises at least one loop formed on said retrieval strand and a button or on said attachment member for engaging said loop.

21. A trauma dressing for intraoral use comprising an absorbent dressing for insertion into the oral cavity of a patient, a flexible, self-supporting retrieval strand having one end securely attached to said absorbent dressing, and an enlarged grip member of sufficient size to prevent its entry into the human oral cavity attached to the other end of said retrieval strand, wherein said grip member has a width of at least three inches in a direction transverse to the longitudinal direction of said retrieval strand.

22. A trauma dressing for intraoral use comprising an absorbent dressing for insertion into the oral cavity of a patient, a flexible, self-supporting retrieval strand having one end securely attached to said absorbent dressing, and an enlarged grip member of sufficient size to prevent its entry into the human oral cavity attached to the other end of said retrieval strand, wherein said retrieval strand comprises a material which will not wick blood.

23. A trauma dressing according to claim 22, wherein said retrieval strand is made of a thermoplastic monofilament.

* * * * *